(12) United States Patent
Wright

(10) Patent No.: US 9,056,868 B1
(45) Date of Patent: Jun. 16, 2015

(54) THREE-STEP SYNTHESIS OF CL-20

(71) Applicant: The United States of America as represented by the Secretary of the Navy, Washington, DC (US)

(72) Inventor: Michael E. Wright, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 14/023,182

(22) Filed: Sep. 10, 2013

Related U.S. Application Data

(60) Provisional application No. 61/700,548, filed on Sep. 13, 2012.

(51) Int. Cl.
*C07D 487/22* (2006.01)

(52) U.S. Cl.
CPC .................................... *C07D 487/22* (2013.01)

(58) Field of Classification Search
USPC ....................................................... 540/554
See application file for complete search history.

(56) References Cited

U.S. PATENT DOCUMENTS

| 5,693,794 | A | 12/1997 | Nielsen |
| 7,875,714 | B1 | 1/2011 | Chapman et al. |
| 8,395,007 | B2 | 3/2013 | Wright et al. |

OTHER PUBLICATIONS

Baltzly, et al., "The effect of substitution on the strength of the O-Benzyl and N-Benzyl linkages." 1943, unknown day and month.
Nielsen, et al., "Poly. by Condensation of aldehydes with amines . . . " J. Org. Chem. 1990, 55, 1459-1466.
Gaunt, et. al. "Rational Design of Benzyl-Type Protecting Groups allows sequential deprotection of Hydroxyl groups by catalytic Hydrogenolysis," J. Org. Chem. 1998, 63, 4172-3.
Klapotke, et al., "Syn. and struct. of Tri., Fluoro-, and Azido-sub. Hexa. and isolation of Novel Hexa . . . based Polycycle." Chem. Eur. J. 2003, 9 No. 3.
Herve, et al. "Preparation and Structure of Novel Hexaazaisowurtzitane." [Chem. Eur. J. 2006, 12, pp. 3339-3344].
Das, et al. Top. Catal. "Selective Catalytic Reductions of Amides and Nitriles to Amines." 2010, 53, pp. 979-984.

*Primary Examiner* — Kristin Vajda
(74) *Attorney, Agent, or Firm* — Charlene A. Haley

(57) ABSTRACT

Embodiments of the invention relate to the synthesis of CL-20 using only a three step synthesis and because of increased catalyst activity and lifetimes, a continuous flow process can be used with a tremendous reduction in total cost of producing CL-20.

13 Claims, 2 Drawing Sheets

THREE-STEP SYNTHESIS OF CL-20

CROSS-REFERENCE TO RELATED APPLICATIONS

This is a non-provisional patent application, claiming the benefit of, parent application Ser. No. 61/700,548 filed on Sep. 13, 2012, whereby the entire disclosure of which is incorporated hereby reference.

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to chemical synthesis of the energetic material CL-20. This invention in particular demonstrates the use of rapid chemical deprotection methods that lead to a highly efficient synthesis of CL-20.

Figure 1:
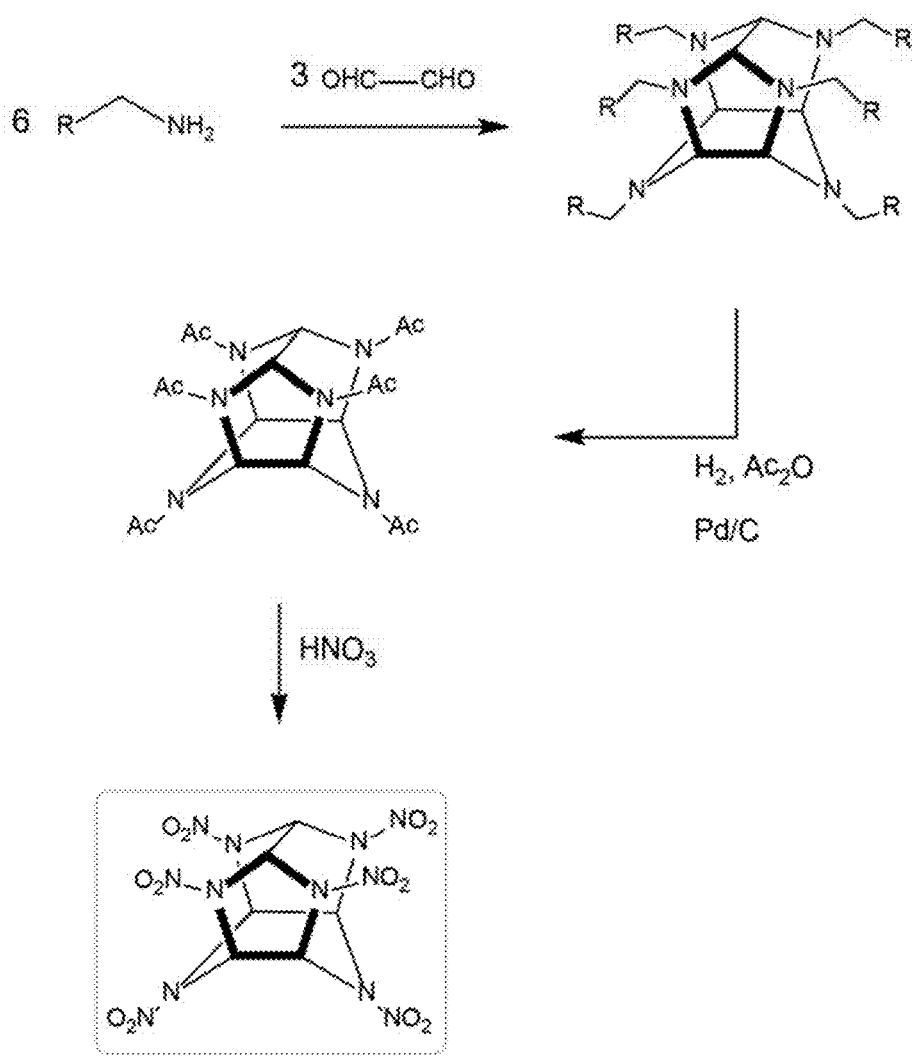
FIG. 1 illustrates the chemical reaction scheme for the conversion of an arylmethyl amine with glyoxal to form the hexa(arylmethyl)hexaazaisowrutzitane, then protecting group exchange to create HAcIW, and then direct conversion to CL-20 by treatment with nitric acid, according to embodiments of the invention.

It is to be understood that the foregoing general description and the following detailed description are exemplary and explanatory only and are not to be viewed as being restrictive of the invention, as claimed. Further advantages of this invention will be apparent after a review of the following detailed description of the disclosed embodiments, which are illustrated schematically in the accompanying drawings and in the appended claims.

The utilization of CL-20 in modern day weapons continues to evolve. What is needed is a relatively low cost and chemically efficient synthesis of the energetic material in order for it to achieve its full potential.

To date there exist several patents and papers that have built upon the original invention of CL-20 discovered at China Lake by Dr. Arnold Nielson (U.S. Pat. No. 5,693,794). Several groups have demonstrated that Hexa(Benzyl)hexaaza-IsoWurtzitane (HBIW) and related derivatives can be prepared using similar condensation chemistry as originally taught by U.S. Pat. No. 5,693,794.

Although several intriguing synthetic routes to CL-20 have been developed over the past two decades, for example Chapman & Hollins U.S. Pat. No. 7,875,714 and references cited therein, it appears that hydrogenative-debenzylation is the chemically most efficient route to a CL-20 precursors. Perhaps the most common and one used in the industrial production of CL-20 is TetraAcetylDiAminohexaazaisowurtzitane (TADA). This latter chemical intermediate is currently the most widely used substrate for direct nitration to obtain CL-20:

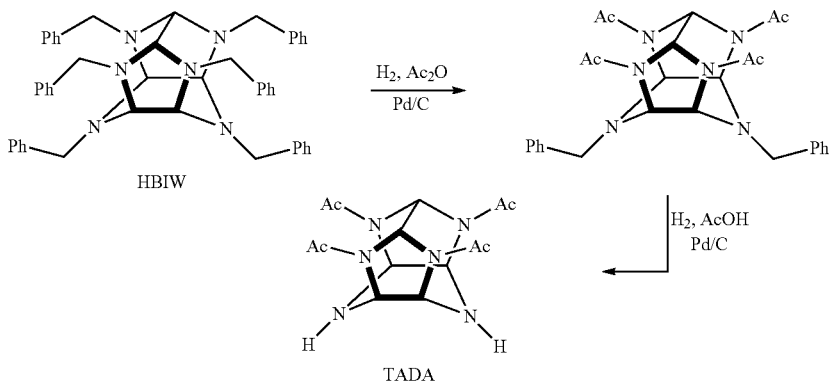

The process above requires two separate hydrogenative-debenzylation reactions and traditionally the ability to recycle the Pd/C is poor. Thus, this process is high cost and demonstrates a poor utilization of natural resources such as, for example, precious metals.

It would be most advantageous to have a hexaazaisowurtzitane precursor that could undergo a single step conversion to TADA or an equivalent that could then be converted directly to CL-20 in a single step. Additionally, the ability to use mild deprotection-reaction conditions would save energy. Furthermore, effective recycling of the precious metal catalyst would teach art that does not presently exist. Embodiments of the invention accomplish all the above and produces an unprecedented and direct route to CL-20 from readily available starting materials and catalysts.

Embodiments of the invention give instant access to a method that gives rapid and complete metathesis of selected benzyl groups acetyl groups in one quick and mild process. The result is the complete recycling of the hydrogenation catalyst, ability to do a continuous flow process, and a reduction in the overall number of chemical steps to prepare CL-20.

A process is disclosed is to prepare new hexa(arenzyl) hexaazaisowuitzitane (HAzIW) where the arenzyl group:

arenzyl group=Aryl-CH$_2$

Where Aryl is a substituted phenyl ring or polycyclic aromatic ring like:

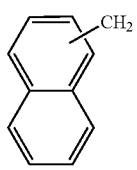

is easily removed at all six positions of the hexaazaisowurtzitane (IW) ring and leads to a direct synthesis of the hexa(acetyl)isowurtzitane (HAcIW). The ability to carry out the reaction under mild conditions and free of activators, like bromobenzene, leads to complete recycle of the precious metal catalyst; hence, a continuous process method is now possible as a result of embodiments of the invention.

A method for recycling the arenyl-methyl co-product from the hydrogenation to provide high chemically efficiency and use of reactants and reagents.

A method for taking the HAcIW directly to CL-20 using nitric acid in a continuous flow system.

A method for collecting the CL-20 from the continuous flow reactor and subjecting it to recrystallization from a mixture of hydrogenated poly alpha-olefins (PAOs) and a suitable alkyl ester such as ethyl acetate. PAOs can be prepared from biobutanol through technology disclosed in NC 99384.

Arylmethyl-amines (ArCH$_2$—NH$_2$) can be prepared in excellent yield through two different routes starting from the respective Arene-CH$_3$ precursor using ammonia and other selected chemical reagents:

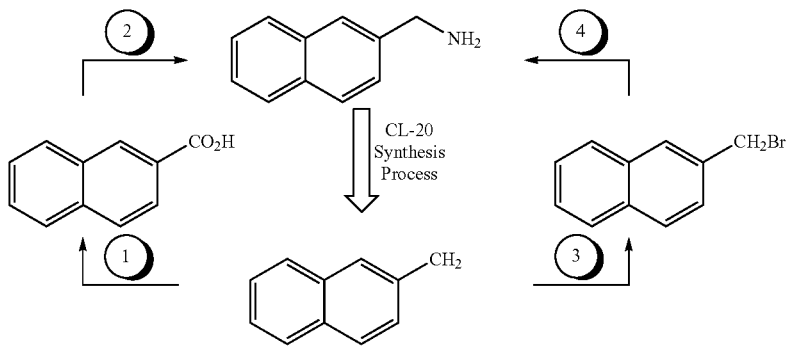

Process 1 involves a catalytic oxidation with air to generate the carboxylic acid. In process 2 the latter is reacted with ammonia at elevated temperature (100-120° C.) to produce the amide and then catalytically reduced to ArCH$_2$—NH$_2$ with hydrogen [Das et al. *Top. Catal.* 2010, 53, pp 979-984]. Another recycling route can be used based on free-radical bromination (Step 3) and then reaction with excess ammonia. Both recycling processes can be done with chemical efficiencies of greater than 80-95% affording lower cost, better atom efficiency, and less waste produced in the overall CL-20 synthesis.

The overall chemical process for converting an arylmethyl-amine (ArCH$_2$—NH$_2$) to CL-20 in three steps is displayed in FIG. 1. The chemistry follows much of the expected pathway reported in previous papers and patents; however, because of the unusual reactivity of HArIW's prepared in embodiments of the invention, a much more efficient and a continuous flow process/synthesis can be realized.

The new H(2-Np)IW can be made using standard procedures developed by Dr. Nielson. An alternative route is to use Lewis acid catalysts such as Lanthanides [e.g. Yb(OTf)$_3$] as recently reported by Herve et al. [*Chem. Eur. J.* 2006, 12, pp. 3339-3344]:

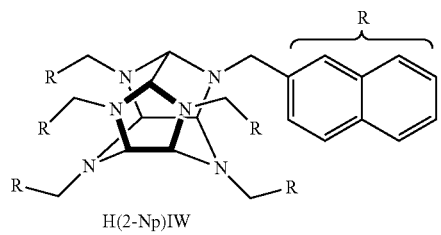

H(2-Np)IW

The H(1-Np)IW has been prepared in the literature although no chemistry has been described for this molecule. In a similar manner, hexa(9-anthracenylmethyl) isohexaazawurtzitane is prepared starting from 9-(aminomethyl)anthracene, glyoxal, and a Lanthanide catalyst.

Figure 2:
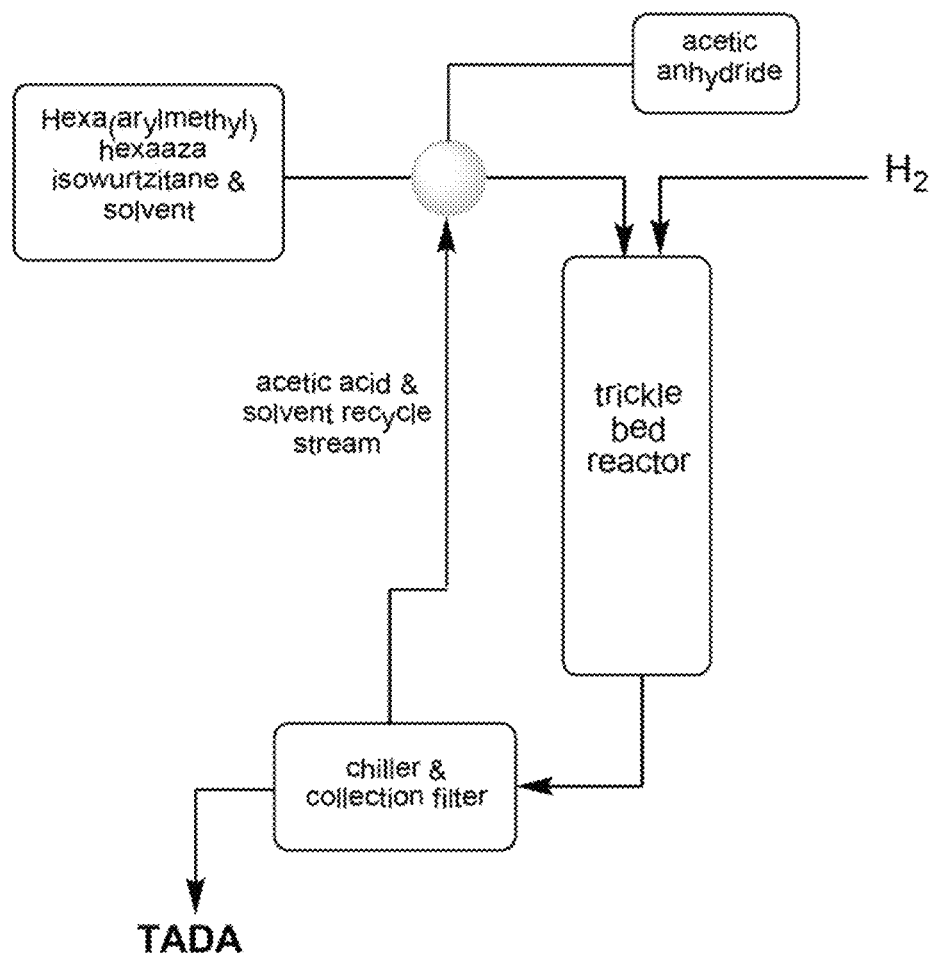
FIG. 2 illustrates a continuous flow process diagram for the synthesis of TADA, according to embodiments of the invention.

The increased reactivity of the aryl-substituents (e.g. H(2-Np)IW) disclosed for the hydrogentative-deprotection provides a rapid, direct, and unexpected access to TADA using very mild reaction conditions (low pressure and temperature) coupled to anticipated yields well above 75-95%. Important is that this embodiment leads to a process that can be done in a continuous flow reactor [FIG. 2] such a trickle-bed catalyst system and avoids the need for batch-catalysis, changing of reaction conditions and reagents (e.g. such as hydrolysis of the acetic anhydride). Furthermore, it also eliminates the need for certain additives (e.g. bromine) that are well known to lead to poor catalyst recovery and often severe catalyst deactivation.

Collection of the TADA from the reactant stream, washing with an inert hydrocarbon solvent, and then conversion to CL-20 by direct nitration in >98% nitric acid. The CL-20 is collected and processed to afford a highly crystalline material with greater than 99.8% pure CL-20.

Final recrystallization of the CL-20 is done using the following process. A mixture of CL-20 is suspended in a mixture of hydrogenated poly alpha-olefins (PAO) obtained from the oligomerization of 1-butene or a mixture of 1-butene and at least one other alpha-olefin. The PAOs should include at least 8 carbons and less than 50 carbon atoms. The average molecular weight of the PAOs can be adjusted to obtain an optimum viscosity of the final recrystallization mixture. The crude CL-20 and PAO is combined with at least one co-solvent. The co-solvents can be selected from ethyl acetate, tetrahydrofuran, dichloroethane, butyl acetate, propyl acetate, or some combination of at least two used in a ratio from 1:10 to 1:1 and their total volume is in the range of 1 to 0.5 compared to the PAO (by volume to volume) Removal of some of the low boiling component under reduced pressure with heating affords a saturated solution of CL-20 in the PAO along with a preselected amount of co-solvent (from the list above) remaining behind. Cooling of the mixture and collection of the CL-20 affords uniform sized crystals (50-200 micron) and importantly in the correct CL-20 epsilon crystal-morphology.

Example 1

A theoretical experimental run: A acetonitrile solution (50 mL) of 2-(aminomethyl)naphthalene (10 g) is treated with glyoxal (4 mol-equiv) and a catalytic amount of formic acid. The mixture is stirred at ambient temperature for a period of 5-24 h and the hexa[(2-naphthyl)methyl]hexaazaisowtzitane (H(2-Np)IW), was collected from the reaction mixture and purified by recrystallization from hot acetonitrile Example 2

A theoretical experimental run: A low pressure bomb was charged with 100 g of H(2-Np)IW, 50 mL of dimethyl acetamide, 20 mL of acetic anhydride, and 1.0 g of 10 wt-% palladium on carbon. The vessel was sealed and charged with 50 psig of hydrogen pressure and allowed to react with stirring for 12 h at 50 deg C. The mixture was filtered hot to first remove the catalyst, next the solution was neutralized, and then allowed to cool. The crystallized TADA was collected by filtration and used in the nitration step to form crude CL-20.

Example 3

A theoretical experimental run: The crude CL-20 (~10 g) was placed in 20 mL of PAO, 20 mL of ethyl acetate, 3 mL of butyl acetate, and then heated for 30 min with stirring. The ethyl acetate was removed under reduced pressure and the solution cooled to ambient temperature. The recrystallized CL-20 was collected and washed with a hydrocarbon solvent, then an alcohol, and finally collected to afford CL-20 of 99.8% purity, 50-200 micron size crystals, and of the epsilon-polymorph.

Embodiments of the invention generally relate to methods for making CL-20 including, preparing hexa(arylmethyl)hexaazaisowurtzitane (A) wherein arylmethyl is selected from the group consisting of 2-naphthylmethyl, 1-naphthylmethyl, 9-anthracenylmethyl, and any combination thereof

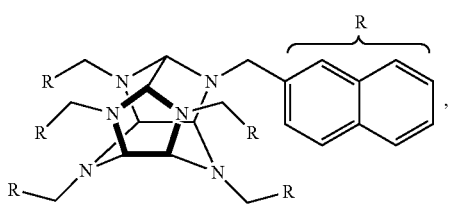

A dissolving the hexa(arylmethyl)hexaazaisowurtzitane in at least one dipolar aprotic solvent and treating with at least one aliphatic anhydride, at least one heterogeneous hydrogenation catalyst, and hydrogen gas while in a closed reaction vessel to form a solution which is allowed to react with heating, removing the heterogeneous hydrogenation catalyst by filtration to afford a filtrate solution, isolating TADA (B) from the filtrate solution by addition of at least one non-solvent, (An isolation technique would include, but is not limited to, evaporating solvents under reduced pressure) treating the TADA with concentrated nitric acid (>98% $HNO_3$).

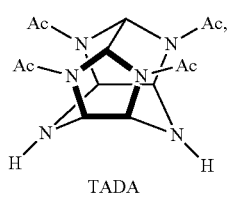

B

TADA and isolating crude CL-20 by dilution with water and collecting the CL-20 by filtration, recrystallizing of the CL-20 by suspension in a solvent mixture having saturated poly alpha-olefins (PAO), and a three solvent system (ethyl acetate, and butyl acetate, THF and other like solvents), removing at least one solvent under reduced-pressure while heating, cooling the solution to about 25° C. to about 30° C., and collecting by filtration to afford about 50-200 micron size crystals of epsilon-CL-20 (C)

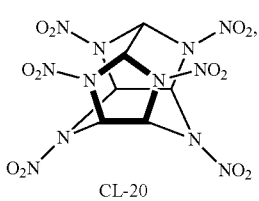

C

CL-20

Another aspect of the invention generally relates to CL-20 produced by the methods herein.

In embodiments, the heterogeneous hydrogenation catalyst is selected from, but not limited to, the group consisting of platinum oxide, 5 wt-% palladium on carbon, 10-wt-% palladium on carbon, and any combination thereof. In embodiments, the aliphatic anhydride is propionic anhydride. In embodiments, the PAO has a range of about 8 carbons atoms to about 50 carbons atoms. In other embodiments, the PAO has a range of about 10 carbons atoms to about 32 carbon atoms. Yet in other embodiments, the PAO has a range of about 12 carbons atoms to about 24 carbon atoms.

In embodiments, at least one dipolar aprotic solvent is selected from, but not limited to, the group consisting of dimethylacetamide, N-methylpyrrolidinone, dimethylformamide, N-cyclohexylpyrrolidinone, and any combination thereof. In embodiments, the aliphatic anhydride is selected from, but not limited to, the group consisting of acetic anhydride, propionic anhydride, butanoic anhydride, and any combination thereof. In embodiments, the closed reaction vessel is a sealed vessel with stirring or continuous flow. In embodiments, the heating is for a period ranging from about 1 hour to about 24 hours. In other embodiments, the treating is with 4 mol-equivalent of an aliphatic anhydride. In embodiments, the removing at least one solvent under reduced-pressure ranging from about 50 torr to about 100 torr while heating ranging from about 25° C. to about 70° C. This time period is a direct function of the equipment utilized but should not be longer than 12 h and with an alternative range of 4 to 8 hours.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A method for making CL-20, comprising:
preparing hexa(arylmethyl)hexaazaisowurtzitane (A) wherein arylmethyl is selected from the group consisting of 2-naphthylmethyl, 1-naphthylmethyl, 9-anthracenylmethyl, and any combination thereof

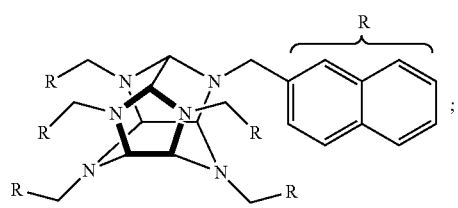

A dissolving said hexa(arylmethyl)hexaazaisowurtzitane in at least one dipolar aprotic solvent and treating with at least one aliphatic anhydride, at least one heterogeneous hydrogenation catalyst, and hydrogen gas while in a closed reaction vessel to form a solution which is allowed to react with heating;
removing said heterogeneous hydrogenation catalyst by filtration to afford a filtrate solution;
isolating TADA (B) from said filtrate solution by addition of at least one non-solvent;

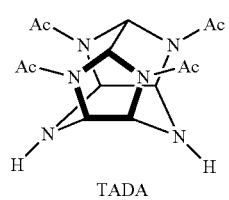

B

TADA treating said TADA with concentrated nitric acid and isolating crude CL-20 by dilution with water and collecting said CL-20 by filtration;
recrystallizing of said CL-20 by suspension in a solvent mixture having saturated poly alpha-olefins (PAO), and a three solvent system, removing at least one of said solvent under reduced-pressure while heating;
cooling said solution to about 25° C. to about 30° C.; and
collecting by filtration to afford about 50-200 micron size crystals of epsilon-CL-20 (C)

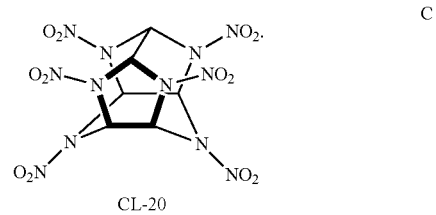

C

CL-20

2. The method according to claim 1, wherein said heterogeneous hydrogenation catalyst is selected from the group consisting of platinum oxide, 5 wt-% palladium on carbon, 10-wt-% palladium on carbon, and any combination thereof.

3. The method according to claim 1, wherein said aliphatic anhydride is propionic anhydride.

4. The method according to claim 1, wherein said PAO has a range of about 8 carbons atoms to about 50 carbons atoms.

5. The method according to claim 1, wherein said PAO has a range of about 10 carbons atoms to about 32 carbon atoms.

6. The method according to claim 1, wherein said PAO has a range of about 12 carbons atoms to about 24 carbon atoms.

7. The method according to claim 1, wherein at least one said dipolar aprotic solvent is selected from the group consisting of dimethylacetamide, N-methylpyrrolidinone, dimethylformamide, N-cyclohexylpyrrolidinone, and any combination thereof.

8. The method according to claim 1, wherein said aliphatic anhydride is selected from the group consisting of acetic anhydride, propionic anhydride, butanoic anhydride, and any combination thereof.

9. The method according to claim 1, wherein said closed reaction vessel is a sealed vessel with stirring or continuous flow.

10. The method according to claim 1, wherein said heating of hydrogen treatment is for a period ranging from about 1 hour to about 24 hours.

11. The method according to claim 1, wherein said treating is with 4 mol-equivalent of an aliphatic anhydride.

12. The method according to claim 1, wherein said removing is at least one of said solvent under reduced-pressure ranging from about 50 torr to about 100 torr while heating ranging from about 25° C. to about 70° C.

13. The method according to claim 1, wherein said three solvent system includes at least one said solvent selected from the group consisting of ethyl acetate, butyl acetate, THF, and other like solvents.

* * * * *